(12) United States Patent
Nappa et al.

(10) Patent No.: US 7,074,973 B2
(45) Date of Patent: Jul. 11, 2006

(54) PROCESS FOR THE PREPARATION OF 1,1,1,2,2-PENTAFLUOROETHANE

(75) Inventors: Mario J. Nappa, Newark, DE (US); Velliyur Nott Mallikarjuna Rao, Wilmington, DE (US); H. David Rosenfeld, Drumore, PA (US); Shekhar Subramoney, Hockessin, DE (US); Munirpallam A. Subramanian, Kennett Square, PA (US); Allen C. Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/523,227

(22) PCT Filed: Aug. 21, 2003

(86) PCT No.: PCT/US03/26324

§ 371 (c)(1),
(2), (4) Date: Jan. 31, 2005

(87) PCT Pub. No.: WO2004/018396

PCT Pub. Date: Mar. 4, 2004

(65) Prior Publication Data

US 2006/0004235 A1 Jan. 5, 2006

Related U.S. Application Data

(60) Provisional application No. 60/405,223, filed on Aug. 22, 2002.

(51) Int. Cl.
*C07C 17/00* (2006.01)

(52) U.S. Cl. .................. 570/169; 570/165; 570/166; 570/168

(58) Field of Classification Search ............... 570/165, 570/166, 168, 169
See application file for complete search history.

(56) References Cited

U.S. PATENT DOCUMENTS

| 3,258,500 | A | 6/1966 | Swamer et al. |
| 3,755,477 | A | 8/1973 | Firth et al. |
| 4,843,181 | A | 6/1989 | Gumprecht et al. |
| 4,967,024 | A | 10/1990 | Gumprecht et al. |
| 5,185,482 | A | 2/1993 | Manzer |
| 5,302,765 | A | 4/1994 | Manzer et al. |

FOREIGN PATENT DOCUMENTS

| AU | A 29972/92 | 6/1993 |
| AU | A 80340/94 | 6/1995 |
| CA | 849024 | 8/1970 |
| CA | 1196345 | 11/1985 |
| EP | 0 641 598 A2 | 3/1995 |
| EP | 0 657 408 A1 | 6/1995 |
| EP | 1 038 858 A1 | 9/2000 |
| WO | WO 98/10862 | 3/1998 |
| WO | WO 2004/018093 A2 | 3/2004 |

OTHER PUBLICATIONS

U.S. Appl. No. 10/523,228, filed Jan. 31, 2005, Rao et al.

*Primary Examiner*—J. Parsa

(57) ABSTRACT

A process for the preparation of pentafluoroethane is disclosed which involves contacting a mixture comprising hydrogen fluoride and at least one starting material selected from haloethanes of the formula $CX_3CHX_2$ and haloethanes of the formula $CX_2=CX_2$, where each X is independently selected from the group consisting of F and Cl (provided that no more than four of X are F), with a fluorination catalyst in a reaction zone to produce a product mixture comprising HF, HCl, pentafluoroethane, underfluorinated halogenated hydrocarbon intermediates and less than 0.2 mole percent chloropentafluoroethane based on the total moles of halogenated hydrocarbons in the product mixture. The process is characterized by the fluorination catalyst comprising (i) a crystalline cobalt-substituted alpha-chromium oxide where from about 0.05 atom % to about 6 atom % of the chromium atoms in the alpha-chromium oxide lattice are replaced by trivalent cobalt ($Co^{+3}$) and/or (ii) a fluorinated crystalline oxide of (i).

2 Claims, No Drawings

PROCESS FOR THE PREPARATION OF 1,1,1,2,2-PENTAFLUOROETHANE

This application represents a national filing under 35 USC 371 of International Application No. PCT/US2003/026324 filed Aug. 21, 2003 claiming priority of U.S. Provisional Application No. 60/405,223 filed Aug. 22, 2002.

FIELD OF THE INVENTION

The present invention relates to the synthesis of 1,1,1,2,2-pentafluoroethane.

BACKGROUND

The compound pentafluoroethane ($CF_3CHF_2$ or HFC-125) is useful as a blowing agent, propellant, refrigerant, fire extinguishing agent, or sterilant carrier gas. It is desirable for its zero ozone depletion potential.

Various methods for the preparation of pentafluoroethane have been disclosed. U.S. Pat. No. 3,755,477 describes a process for producing fluorinated hydrocarbons using a chromia catalyst prepared by treating a chromium hydroxide paste with water or steam before it is dried and calcined. Example 23 illustrates the conversion of tetrachloroethylene to a product mixture containing $CF_3CHCl_2$ (20%), $CF_3CHClF$ (20%), $CF_3CHF_2$ (30%), and $CF_3CClF_2$ (20%); and Example 25 illustrates the conversion of $CF_3CHCl_2$ to a product mixture containing $CF_3CHClF$ (21%), $CF_3CHF_2$ (67%) and $CF_3CClF_2$ (2.5%). Chloropentafluoroethane ($CF_3CClF_2$ or CFC-115) is objectionable because it represents a yield loss and it is difficult to separate from pentafluoroethane by distillation.

U. S. Pat. No. 3,258,500 describes a process for the catalytic vapor-phase fluorination of certain halohydrocarbons employing a catalyst that consists essentially of an activated anhydrous chromium (III) oxide. Example 17 illustrates the conversion of tetrachloroethylene to a product mixture containing inter alia $CF_3CHCl_2$ (3.5%), $CF_3CHClF$ (9.2%), and $CF_3CHF_2$ (35.0%) at 400° C. and to a product mixture containing inter alia $CF_3CHCl_2$ (16.0%), $CF_3CHClF$ (38.3%), and $CF_3CHF_2$ (25.4%) at 300° C.; and Example 20 illustrates the conversion of chlorotrifluoroethylene to a product mixture containing inter alia $CF_3CHF_2$ (26.8%) at 400° C.

Canadian Patent 849,024 and Canadian Patent 1,196,345 also disclose processes employing chromium-containing catalysts that may be used to produce pentafluroethane.

U. S. Pat. No. 4,843,181 discloses a gas phase process for the manufacture of $CF_3CHCl_2$ and/or $CF_3CHClF$ by contacting a suitable tetrahaloethylene and/or pentahaloethane with HF in the presence of $Cr_2O_3$ prepared by the pyrolysis of $(NH_4)_2Cr_2O_7$, the reaction being conducted under controlled conditions whereby the production of $CF_3CClF_2$ is minimized.

There is a need for other useful methods of preparing $CF_3CHF_2$ where the amount of chloropentafluoroethane by-product is low.

SUMMARY OF THE INVENTION

This invention provides a process for the preparation of pentafluoroethane. The process comprises contacting a mixture comprising hydrogen fluoride (HF) and at least one one starting material selected from haloethanes of the formula $CX_3CHX_2$ and haloethenes of the formula $CX_2=CX_2$, where each X is independently selected from the group consisting of F and Cl provided that no more than four of X are F, with a fluorination catalyst in a reaction zone to produce a product mixture comprising HF, HCl, pentafluoroethane, underfluorinated halogenated hydrocarbon intermediates and less than 0.2 mole percent chloropentafluoroethane based on the total moles of halogenated hydrocarbons in the product mixture. The process is characterized by said fluorination catalyst comprising at least one chromium-containing component selected from (i) a crystalline cobalt-substituted alpha-chromium oxide where from about 0.05 atom % to about 6 atom % of the chromium atoms in the alpha-chromium oxide lattice are replaced by trivalent cobalt ($Co^{+3}$), and (ii) a fluorinated crystalline oxide of (i).

DETAILED DESCRIPTION

In the fluorination step of the process of this invention, one or more haloethane compound(s) of the formula $CX_3CHX_2$, or one or more haloethene compound(s) of the formula $CX_2=CX_2$, or a mixture thereof, where each X is independently selected from the group consisting of F and Cl (provided that no more than four of X are F) are typically reacted with substantially anhydrous hydrogen fluoride (HF). Suitable halogenated starting materials for the process of this invention include $CCl_2=CCl_2$, $CClF=CCl_2$, $CClF=CClF$, $CF_2=CCl_2$, $CClF=CF_2$, $CF_2=CF_2$, $CHCl_2CCl_3$, $CHCl_2CCl_2F$, $CHClFCCl_3$, $CHCl_2CClF_2$, $CHClFCCl_2F$, $CHF_2CCl_3$, $CHClFCClF_2$, $CHCl_2CF_3$, $CHF_2CClF_2$, and $CHClFCF_3$. Preferred starting materials are $CCl_2=CCl_2$, $CHCl_2CF_3$, and $CHClFCF_3$. Tetrachloroethene is an available item of commerce. 2,2-Dichloro-1,1,1-trifluoroethane may be prepared by the reaction of tetrachloroethene with HF in the presence of tantalum pentafluoride as disclosed by Gumprecht and Schindel in U. S. Pat. No. 4,967,024. 2-Chloro-1,1,1,2-tetrafluoroethane may be prepared by chlorination of 1,1,1,2-tetrafluoroethane as disclosed by Manzer et. al. in U.S. Pat. No. 5,302,765.

Preferably, the reaction of HF and with haloethanes and haloethenes is carried out in the vapor phase in a heated tubular reactor. A number of reactor configurations are possible including horizontal or vertical orientation of the reactor and different modes of contacting the halogenated starting materials with HF.

In one embodiment of the invention, the organic starting material(s) may be initially vaporized and fed to the reactor as gas(es).

In another embodiment of the invention, the organic starting material(s) may be contacted with HF in a pre-reactor. The pre-reactor may be empty, but is preferably filled with a suitable packing such as Monel™ or Hastelloy™ nickel alloy turnings or wool, or other material inert to HCl and HF which allows for efficient mixing of haloethane or haloethene and HF vapor.

Suitable temperatures for the pre-reactor are within the range of from about 80° C. to about 250° C., preferably from about 100° C. to about 200° C. For haloethane and haloethene starting materials having fewer than three fluorine substituents, some substitution of chlorine substituents by fluorine may occur in the pre-reactor. Higher temperatures result in greater conversion of the $CX_3CHX_2$ and $CX_2=CX_2$ entering the reactor and a greater degree of fluorination in the converted products. Under these conditions, for example, tetrachloroethene may be converted to a mixture containing predominantly $CHCl_2CCl_2F$ and $CHCl_2CClF_2$.

The term "degree of fluorination" reflects the number of fluorine substituents that replace chlorine substituents in the $CX_3CHX_2$ and $CX_2=CX_2$ starting materials. For example, $CF_3CHF_2$ represents a higher degree of fluorination than $CF_3CHCl_2$ and $CF_2=CCl_2$ represents a higher degree of fluorination than $CCl_2=CCl_2$. The term "underfluorinated halogenated hydrocarbon intermediates" means haloethanes of the formula $CX_3CHX_2$ wherein at least one X is Cl, and haloethenes of the formula $CX_2=CX_2$. Examples of underfluorinated intermediates are $CCl_2=CCl_2$, $CClF=CCl_2$, $CClF=CClF$, $CF_2=CCl_2$, $CClF=CF_2$, $CF_2=CF_2$, $CHCl_2CCl_3$, $CHCl_2CCl_2F$, $CHClFCCl_3$, $CHCl_2CClF_2$, $CHClFCCl_2F$, $CHF_2CCl_3$, $CHClFCClF_2$, $CHCl_2CF_3$, $CHF_2CCl_2$, and $CHClFCF_3$ (i.e., the same compounds suitable as starting materials). Underfluorinated halgenated hydrocarbon intermediates may include unreacted starting material, but do not include either pentafluoroethane (i.e., the desired product) or chloropenffluoroethane (i.e., an undesireable by-product).

The molar ratio of HF to $CX_3CHX_2$ and $CX_2=CX_2$ starting material(s) in the pre-reactor is typically from about the stoichiometric ratio of HF to $CX_3CHX_2$ and $CX_2=CX_2$ to about 40:1. The stoichiometric ratio of HF to the starting material depends on the whether the starting materials is a haloethane or a haloethene, or a mixture, and the average degree of fluorination of the starting material(s) fed to the pre-reactor. For example, if the starting material is $CCl_2=CCl_2$, the stoichiometric ratio of HF to $CCl_2=CCl_2$ is 5:1 for formation of $CF_3CHF_2$; if the starting material is $CF_3CHCl_2$, the stoichiometric ratio of HF to $CF_3CHCl_2$ is 2:1. Preferably, the molar ratio of HF to starting material in the pre-reactor is from about twice the stoichiometric ratio of HF to haloethane or haloethene to about 15:1. Higher molar ratios of HF to starting material are not particularly beneficial. Lower ratios result in reduced yields of HFC-125 unless additional HF is co-fed to the reaction zone.

In a preferred embodiment of the invention, in step (a) the $CX_3CHX_2$ and $CX_2=CX_2$ starting material(s) are vaporized, preferably in the presence of HF, and then fed to the reactor zone. If he preferred amounts of HF are fed in the pre-reactor, additional HF is not required in the reaction zone.

The contacting of the organic starting materials with HF in the presence of the catalyst, preferably pretreated, of the instant invention in the reaction zone is performed at an effective temperature, mole ratio and contact time. By effective temperature, mole ratios and contact times is meant the temperatures, mole ratios and contact times which produce a product stream which contains $CF_3CHF_2$ in a major proportion, preferably in an amount of at least 50 mole %, more preferably at least about 60 mole %, as determined by gas chromatography.

With $CF_3CHCl_2$ or $CF_3CHClF$ as the reactant, the temperature will normally range from about 300° C. to about 380° C., preferably about 330° C. to 350° C. The HF/organic mole ratio will normally range from about 1.5/1 to about 10/1, preferably from about 2/1 to 8/1. The contact time will vary widely but preferably will be such as to provide an average residence time of from 2 to 100 seconds, and more preferably 10 to 50 seconds.

The pressure is not critical but should be sufficient to maintain HF, the organic reactant and the reactant product stream components in the vapor state at the operating temperature. Reactor pressures of about 5 atmospheres to about 30 atmospheres may be advantageously employed to facilitate separation of HCl from other reaction products in step (b) of the process.

In general, the higher the temperature, the greater the HF/organic mole ratio, and the longer the contact time, the greater is the conversion of the reactants to fluorinated products, and the greater is the degree of fluorination of the raw material. The above variables can be balanced, one against the other, so that formation of $CF_3CHF_2$ is maximized and that of perhalogenated by-products is minimized, preferably to less than about 3%, with that of $CClF_2CF_3$ to less than 2%, more preferably to less than 1%, and most preferably less than 0.2%, said percents being mole percents as determined by gas chromatography.

This process allows unreacted starting material and other underfluorinated intermediates to be recycled to the reactor for the production of additional $CF_3CHF_2$. For example, the fluorination step (step (a)) may be advantageously followed by a separation step (step(b)) separating the product of step (a) to recover $CF_3CHF_2$ as a product and to obtain underfluorinated halogenated hydrocarbon intermediates; and a recycle step (step (c)) returning underfluorinated halogenated hydrocarbon intermediates obtained in step (b) back to the step (a) reaction zone.

In step (b) the effluent from the reaction zone in step (a) comprising $CF_3CHF_2$, HCl, HF, and the underfluorinated halogenated ethanes and ethenes, is delivered to one or more separation zones in which $CF_3CHF_2$ is separated from the HCl, excess HF, and underfluorinated halogenated ethanes and ethenes. The separation zones may comprise conventional chemical processing equipment such as, but not limited to, scrubbers, decanters, and/or distillation columns. The pentafluoroethane is recovered.

In step (c) of the process of this invention, underfluorinated halogenated ethanes and ethenes, as well as excess HF obtained in the separation zone(s) may be returned to step (a). Limited amounts of pentafluoroethane and chloropentafluoroethane may also be returned to the reaction zone as long as the product mixture contains less than 0.2 mole percent chloropentafluoroethane based on the total moles of halogenated hydrocarbons therein.

Of note are embodiments where $CCl_2=CCl_2$ is used as the starting material and a recycle comprising $CHCl_2CF_3$, $CHClFCF_3$ or both $CHCl_2CF_3$ and $CHClFCF_3$ is returned to the reaction zone in step (c).

The reaction zone in the fluorination step (e.g., step (a)) of the process of the invention may contain a fluorination catalyst comprising a crystalline cobalt-substituted alpha chromium oxide where from about 0.05% to about 6% of the chromium in the alpha-chromium oxide lattice is replaced by trivalent cobalt ($Co^{+3}$) based on the total of the cobalt and chromium in the alpha-chromium oxide. These cobalt-substituted alpha-chromium oxides have the general formula $\alpha\text{-}Co_xCr_{2-x}O_3$ where x=0.001–0.12. Crystalline oxides of this formula may be fluorinated before use in the reaction zone. Further information on cobalt-substituted alpha-chromium oxides useful for this invention is provided in U.S. Patent Application 60/405,220 [CL2099 US PRV] filed Aug. 22, 2002, and hereby incorporated by reference herein in its entirety.

These cobalt/chromium oxide compositions may be prepared by co-precipitation from aqueous solutions of cobalt (II) and chromium(III) salts. Preferably, the cobalt and chromium salts are co-precipitated by adding ammonium hydroxide (aqueous ammonia) to an aqueous solution of a soluble divalent cobalt salt and a soluble trivalent chromium salt wherein the concentration of divalent cobalt is from about 0.05 mole % to about 6 mole % of the total of cobalt and chromium in the solution, said solution containing at least three moles of nitrate (i.e., $NO_3^{31}$ ) per total mole of chromium (i.e., $Cr^{3+}$) and at least three moles of ammonium (i.e., $NH_4^+$) per mole of chromium (i.e., $Cr^{3+}$) before the co-precipitated solid is collected. After precipitation is complete, water is evaporated from the mixture, and the resulting solid is dried and calcined as discussed in the co-pending patent application referenced above.

Of note are preparations where excess ammonium nitrate (i.e., more than three moles of ammonium nitrate per mole of chromium) is present in the aqueous solution. For example, in addition to the ammonium nitrate already present from reaction of ammonium hydroxide with chromium nitrate, from about 0.1 mole to about 7.0 moles of additional ammonium nitrate per mole of chromium may be added to the solution before, during, or after the co-precipitation of the compositions. Surprisingly, we have found that addition of excess ammonium nitrate to the precipitated mixture of cobalt and chromium hydroxides prior to the dehydration step may be used to decrease the particle size of the $\alpha$-Co$_x$Cr$_{2-x}$O$_3$ phase which in turn increases the surface area of that phase and the activity of the catalyst (see PREPARATION EXAMPLES 5 and 6). The ammonium nitrate treatment also tends to increase the selectivity of the final cobalt/chromium oxide catalyst (see EXAMPLES 2, 3, 6, 9, 15, 16, 17, and 18).

After the ammonium nitrate is added to the mixture, it is preferably stirred for about 0.5 to ten hours (more preferably one to five hours) at a temperature of from about 20° C. to about 60° C. The mixture is then dried and calcined.

Other agents that serve this purpose include aqueous hydrogen peroxide (1% to 30% solutions), ozone, peroxy acids such as peroxyacetic acid, and ammonium persulfate. Agents such as halogens may be used, but are not preferred. Agents containing alkali metals such as potassium persulfate or sodium perborate may also be used but are not preferred.

After the precipitation of the mixture of cobalt and chromium hydroxides is complete, and excess ammonium nitrate or other agents added if desired, the mixture is dried by evaporation.

Optionally, the precipitated mixture of cobalt and chromium hydroxide may be collected and, if desired, washed with deionized water before drying. This may influence the activity of the catalyst.

After the cobalt and chromium hydroxide mixture has been dried, the nitrate salts are then decomposed by heating the solid from about 250° C. to about 350° C. The resulting solid is then calcined at temperature of from about 375° C. to about 1000° C., preferably from about 400° C. to about 600° C. Lower calcination temperatures may result in the presence of some residual nitrate impurities in the metal oxide. The calcination temperature can influence the activity of the catalysts. The calcination is preferably carried out in the presence of oxygen, most preferably in the presence of air.

After calcination, the resulting metal-substituted crystallites are not visually distinguishable from $\alpha$-Cr$_2$O$_3$ by transmission electron microscopy. Furthermore, X-ray and electron diffraction studies are entirely consistent with the $\alpha$-Cr$_2$O$_3$ structure with some lattice contraction proportional to the amount of Co(III) substituted for Cr(III) in the $\alpha$-Cr$_2$O$_3$ structure. Further details on the characterization of these compositions are provided in the concurrently filed patent application referenced above and incorporated herein by reference.

The cobalt content of the chromium oxide compositions of the present invention effects the activity of the catalyst obtained after fluorinating the mixed metal oxide. For example, the data in Table 1 shows that substitution of Co$^{+3}$ into the $\alpha$-Cr$_2$O$_3$ lattice, particularly in the range of 1–2%, results in a catalyst with comparable or higher activity relative to chromium oxide which does not contain cobalt. In addition, partial substitution of Co$^{+3}$ for Cr$^{+3}$ in the $\alpha$-Cr$_2$O$_3$ lattice results in a catalyst that produces low amounts of CFC-115. Higher cobalt loadings reduce the activity of the catalyst. Furthermore, in accord with the teachings of this invention the performance of a catalyst composition containing a given ratio of cobalt to chromium may be enhanced by treating the initial solution of cobalt(II) and chromium (III) nitrates with an agent such as ammonium nitrate prior to dehydration and calcination.

TABLE 1

Activity of Fluorinated Cobalt/Chromium Oxides for Fluorination of CHClFCF$_3$ to CHF$_2$CF$_3$[a]

| Cr/Co Ratio | CF$_3$CClF$_2$ (ppm) in 70% 125 in exit | % CF$_3$CHF$_2$ in Product at 330° C. |
|---|---|---|
| 100/0 | 1000 | 66 |
| 99/1 | 420 | 67 |
| 98/2 | 210 | 70 |
| 98/2 | 550 | 62[b] |
| 97/3 | 830 | 48 |
| 95/5 | 574 | 56 |
| 95/5 | 1000 | 55[b] |
| 95/5 excess NH$_4$NO$_3$ | 447 | 58 |
| 90/10 | —[c] | 13 |
| 90/10 excess NH$_4$NO$_3$ | —[c] | 48 |

[a]Catalysts were prepared by co-precipitation technique using ammonia.
[b]Separate catalyst preparation.
[c]Catalyst not active enough to generate 70% 125 in effluent. As suggested in U.S. Patent Application 60/405,220 [CL2099 US PRV] filed Aug. 22, 2002, these catalysts may be expected to differ significantly from compositions containing lower proportions of Co due to the solubility limit of Co in alpha chromium oxide.

The catalyst compositions used in the process of this invention may further comprise one or more additives in the form of metal compounds that alter the selectivity or activity of the crystalline cobalt-substituted alpha chromium oxides or the fluorinated metal oxide catalysts containing cobalt and chromium. Suitable additives may be selected from the group consisting of fluoride, oxide, or oxyfluoride compounds of Mg, Ca, Sc, Y, La, Ti, Zr, Hf, V, Nb, Ta, Mo, W, Mn, Re, Fe, Ru, Co, Rh, Ir, Ni, Pd, Pt, Cu, Ag, Au, Ce, and Zn.

The total content of metal compound additive(s) in the catalyst compositions used in the present invention may be up to about 15 atom % based on the total metal content of the compositions (e.g. from about 0.05 atom % to 5 atom %). The additives may be incorporated into the compositions of the present invention by standard procedures.

Generally, the calcined compositions will be pre-treated with a fluorinating agent prior to use as catalysts for changing the fluorine content of halogenated carbon compounds. Accordingly, the reaction zone in the fluorination step (e.g., step (a)) of the process of the invention may contain a fluorination catalyst comprising a fluorinated crystalline cobalt-substituted alpha chromium oxide (where from about 0.05% to about 6% of the chromium in the alpha-chromium oxide lattice is replaced by trivalent cobalt based on the total of the cobalt and chromium in the alpha-chromium oxide). Typically this fluorinating agent is HF though other materials may be used such sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pre-treatment is not essential.

The reaction zone and its associated feed lines, effluent lines, and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The product of this invention, 1,1,1,2,2-pentafluoroethane (HFC-125), is useful as a refrigerant and fire extinguishant.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Catalyst Preparations

Comparative Preparation Example 1

Preparation of 100% Chromium Catalyst (400° C.)

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The resulting solid was then calcined in air at 400° C. for 24 hours.

Preparation Example 2

Preparation of 99% Chromium/1% Cobalt Catalyst (400° C.)

A solution of 792.29 g $Cr(NO_3)_3[9(H_2O)]$ (1.98 moles) and 5.82 g $Co(NO_3)_2[6(H_2O)]$ (0.0200 mole) was prepared in 2000 mL of deionized water. The solution was treated dropwise with 955 mL of 7.4M aqueous ammonia which raised the pH to about 8.5. The slurry was stirred at room temperature overnight. The pH was adjusted to 8.5 the following day. The solid was then collected using two fritted funnels; the resulting solid in each funnel was washed with 15–20 liters of deionized water. The solids were dried in air at 120° C. for 24 hours and then calcined in air at 400° C. for 24 hours.

Preparation Example 3

Preparation of 98% Chromium/2% Cobalt Catalyst (400° C.)

A solution of 784.30 g $Cr(NO_3)_3[9(H_2O)]$ (1.96 moles) and 11.64 g $Co(NO_3)_2[6(H_2O)]$ (0.040 mole) was prepared in 2000 mL of deionized water. The solution was treated dropwise with 950 mL of 7.4M aqueous ammonia which raised the pH from about 1.8 to about 8.5. The slurry was stirred at room temperature overnight and then evaporated to dryness in air at 110–120° C. for 48 hours. The dried catalyst was divided in half. One half was calcined in air at 400° C. for 24 hours.

Preparation Example 4

Preparation of 95% Chromium/5% Cobalt Catalyst (1.6 eq. of excess $NH_4NO_3$, 400° C.)

A solution of 760.28 g $Cr(NO_3)_3[9(H_2O)]$ (1.90 moles) and 29.10 g $Co(NO_3)_2[6(H_2O)]$ (0.10 mole) was prepared in 2000 mL of deionized water. The solution was treated dropwise with 950 mL of 7.4M aqueous ammonia; the pH reached 8.5. The slurry was stirred at room temperature for 24 hours and then treated with a solution of 240.12 g $NH_4NO_3$ (3.0 moles). After stirring at room temperature for 2 hours, the mixture was evaporated to dryness in air at 120° C. and held at that temperature over the weekend. The dried catalyst was ground to a powder with a mortar and pestle and then calcined in air at 400° C. for 24 hours.

Preparation Example 5

Preparation of 90% Chromium/10% Cobalt Catalyst (washed; 400° C.)

A solution of 720.27 g $Cr(NO_3)_3[9(H_2O)]$ (1.80 moles) and 58.21 g $Co(NO_3)_2[6(H_2O)]$ (0.20 mole) was prepared in 2000 mL of deionized water. The solution was treated dropwise with 955 mL of 7.4M aqueous ammonia which raised the pH from about 2.1 to about 8.5. The slurry was stirred at room temperature overnight. The following day, the pH was the increased from 8.05 to 8.5 by addition of aqueous ammonia. The solid was collected in two 3 L fritted funnels and each portion washed with 15–20 L of deionized water. The washed solid was then evaporated to dryness in air at 120° C. for 24 hours. The dried catalyst was then calcined in air at 400° C. for 24 hours.

Preparation Example 6

Preparation of 90% Chromium/10% Cobalt Catalyst (6.7 eq. of excess $NH_4NO_3$, 400° C.)

A solution of 72.03 g $Cr(NO_3)_3[9(H_2O)]$ (0.18 mole) and 5.82 g $Co(NO_3)_2[6(H_2O)]$ (0.020 mole) was prepared in 200 mL of deionized water. The solution was brought to pH 8.5 treatment with 7.4M aqueous ammonia. The slurry was stirred at room temperature for 24 hours. The mixture was then treated with a solution of 96.05 g of $NH_4NO_3$ (1.2 moles) dissolved in 200 mL of water. The slurry was stirred for one hour and then dried at 120° C. in air for about 90 hours. The dried solids was crushed to a powder and then placed in covered dish and calcined at 400° C. for 24 hours in air.

General Procedure for Fluorocarbon Product Analysis

The following general procedure is illustrative of the method used for analyzing the products of fluorocarbon reactions. Part of the total reactor effluent was sampled on-line for organic product analysis using a gas chromatograph equipped with a mass selective detector (GC-MS). The gas chromatography was accomplished with a 20 ft. (6.1 m) long×⅛ in. (0.32 cm) diameter tubing containing Krytox® perfluorinated polyether on an inert carbon support.

The helium flow was 30 mL/min ($5.0 \times 10^{-7}$ m³/s). Gas chromatographic conditions were 60° C. for an initial hold period of three minutes followed by temperature programming to 200° C. at a rate of 6° C./minute.

The bulk of the reactor effluent containing organic products and also inorganic acids such as HCl and HF was treated with aqueous caustic prior to disposal.

All vapor reactions were conducted at a nominal pressure of one atmosphere.

| Legend | |
|---|---|
| 113 is $CCl_2FCClF_2$ | 114a is $CF_3CCl_2F$ |
| 115 is $CF_3CClF_2$ | 123 is $CHCl_2CF_3$ |
| 124 is $CHClFCF_3$ | 124a is $CHF_2CClF_2$ |
| 125 is $CHF_2CF_3$ | 133a is $CH_2ClCF_3$ |
| CT is contact time | |

Comparative Example 1

Chromium oxide (6.05 g, 4 mL, 12–20 mesh, (1.68 to 0.84 mm)), prepared as described in COMPARATIVE PREPARATION EXAMPLE 1 was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m³/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m³/s) and HF was then admitted to the reactor at a flow rate of 12 cc/min ($2.0 \times 10^{-7}$ m³/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m³/s) and the flow of HF was increased to 28 cc/min ($4.7 \times 10^{-7}$ m³/s). After 20 minutes, the flow of nitrogen was reduced to 5 cc/min ($8.3 \times 10^{-8}$ m³/s) and the flow of HF was increased to 36 cc/min ($6.0 \times 10^{-7}$ m³/s). After 20 minutes, the flow of nitrogen was shut off and the flow of HF was increased to 40 cc/min ($6.7 \times 10^{-7}$ m³/s), and this condition was maintained for 120 minutes. The reactor temperature was adjusted to 350° C. and HF and HCFC-124 vapor were fed to the reactor in molar ratio of 2:1 at a contact time of 3.3 seconds. The GC-MS analysis of the reactor effluent is given below.

| Component | Mole % |
|---|---|
| HFC-125 | 77.9 |
| CFC-115 | 2400 ppm |
| HCFC-124 | 12.8 |
| HCFC-124a | 0.5 |
| CFC-114a | 0.2 |
| HCFC-123 | 7.9 |
| CFC-113 | 0.1 |

Comparative Example 2

Cobalt-substituted chromium oxide (Cr/Co 90/10, 6.75 g, 4 mL, 12–20 mesh, (1.68 to 0.84 mm)), prepared as described in PREPARATION EXAMPLE 5 was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m³/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m³/s) and HF was then admitted to the reactor at a flow rate of 12 cc/min ($2.0 \times 10^{-7}$ m³/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m³/s) and the flow of HF was increased to 28 cc/min ($4.7 \times 10^{-7}$ m³/s). After 20 minutes, the flow of nitrogen was reduced to 5 cc/min ($8.3 \times 10^{-8}$ m³/s) and the flow of HF was increased to 36 cc/min ($6.0 \times 10^{-7}$ m³/s). After 20 minutes, the flow of nitrogen was shut off and the flow of HF was increased to 40 cc/min ($6.7 \times 10^{-7}$ m³/s), and this condition was maintained for 120 minutes. The reactor temperature was adjusted to 350° C. and HF and HCFC-124 vapor were fed to the reactor in molar ratio of 2:1 at a contact time of 3.3 seconds. The GC-MS analysis of the reactor effluent is given below.

| Component | Mole % |
|---|---|
| HFC-125 | 19.1 |
| CFC-115 | 48 ppm |
| HCFC-124 | 77.5 |
| HCFC-124a | 0.4 |
| HCFC-123 | 3.0 |

Comparative Example 3

Cobalt-substituted chromium oxide (Cr/Co 90/10, 5.66 g, 4 mL, 12–20 mesh, (1.68 to 0.84 mm)), prepared as described in PREPARATION EXAMPLE 6 was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m³/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m³/s) and HF was then admitted to the reactor at a flow rate of 12 cc/min ($2.0 \times 10^{-7}$ m³/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m³/s) and the flow of HF was increased to 28 cc/min ($4.7 \times 10^{-7}$ m³/s). After 20 minutes, the flow of nitrogen was reduced to 5 cc/min ($8.3 \times 10^{-8}$ m³/s) and the flow of HF was increased to 36 cc/min ($6.0 \times 10^{-7}$ m³/s). After 20 minutes, the flow of nitrogen was shut off and the flow of HF was increased to 40 cc/min ($6.7 \times 10^{-7}$ m³/s), and this condition was maintained for 120 minutes. The reactor temperature was adjusted to 350° C. and HF and HCFC-124 vapor were fed to the reactor in molar ratio of 2:1 at a contact time of 3.3 seconds. The GC-MS analysis of the reactor effluent is given below.

| Component | Mole % |
|---|---|
| HFC-125 | 62.0 |
| CFC-115 | 200 ppm |
| HCFC-124 | 23.3 |
| HCFC-124a | 0.2 |
| HCFC-133a | 0.3 |
| FCFC-114a | 0.1 |
| HCFC-123 | 14.0 |
| FCFC-113 | 0.1 |

Example 4

Cobalt-substituted chromium oxide (Cr/Co 99/1, 5.96 g, 4 mL, 12–20 mesh, (1.68 to 0.84 mm)), prepared as described in PREPARATION EXAMPLE 2 was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m$^3$/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m$^3$/s) and HF was then admitted to the reactor at a flow rate of 12 cc/min ($2.0 \times 10^{-7}$ m$^3$/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m$^3$/s) and the flow of HF was increased to 28 cc/min ($4.7 \times 10^{-7}$ m$^3$/s). After 20 minutes, the flow of nitrogen was reduced to 5 cc/min ($8.3 \times 10^{-8}$ m$^3$/s) and the flow of HF was increased to 36 cc/min ($6.0 \times 10^{-7}$ m$^3$/s). After 20 minutes, the flow of nitrogen was shut off and the flow of HF was increased to 40 cc/min ($6.7 \times 10^{-7}$ m$^3$/s), and this condition was maintained for 120 minutes. The reactor temperature was adjusted to 350° C. and HF and HCFC-124 vapor were fed to the reactor in molar ratio of 2:1 at a contact time of 3.3 seconds. The GC-MS analysis of the reactor effluent is given below.

| Component | Mole % |
|---|---|
| HFC-125 | 76.2 |
| CFC-115 | 1400 ppm |
| HCFC-124 | 13.5 |
| HCFC-124a | 0.2 |
| HCFC-133a | 0.4 |
| CFC-114a | 0.2 |
| HCFC-123 | 9.2 |
| CFC-113 | 0.1 |

Example 5

Cobalt-substituted chromium oxide (Cr/Co 98/2, 5.77 g, 4 mL, 12–20 mesh, (1.68 to 0.84 mm)), prepared as described in PREPARATION EXAMPLE 3 was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m$^3$/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m$^3$/s) and HF was then admitted to the reactor at a flow rate of 12 cc/min ($2.0 \times 10^{-7}$ m$^3$/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m$^3$/sx10$^{-7}$ m$^3$/s) and the flow of HF was increased to 28 cc/min ($4.7 \times 10^{-7}$ m$^3$/s). After 20 minutes, the flow of nitrogen was reduced to 5 cc/min ($8.3 \times 10^{-8}$ m$^3$/s) and the flow of HF was increased to 36 cc/min ($6.0 \times 10^{-7}$ m$^3$/s). After 20 minutes, the flow of nitrogen was shut off and the flow of HF was increased to 40 cc/min ($6.7 \times 10^{-7}$ m$^3$/s), and this condition was maintained for 120 minutes. The reactor temperature was adjusted to 350° C. and HF and HCFC-124 vapor were fed to the reactor in molar ratio of 2:1 at a contact time of 3.3 seconds. The GC-MS analysis of the reactor effluent is given below.

| Component | Mole % |
|---|---|
| HFC-125 | 74.8 |
| CFC-115 | 780 ppm |
| HCFC-124 | 14.9 |
| HCFC-124a | 0.2 |
| HCFC-133a | 0.3 |
| CFC-114a | 0.2 |
| HCFC-123 | 9.5 |
| CFC-113 | 0.1 |

Example 6

Cobalt-substituted chromium oxide (Cr/Co 95/5, 5.95 g, 4 mL, 12–20 mesh, (1.68 to 0.84 mm)), prepared as described in PREPARATION EXAMPLE 4 was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m$^3$/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m$^3$/s) and HF was then admitted to the reactor at a flow rate of 12 cc/min ($2.0 \times 10^{-7}$ m$^3$/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m$^3$/s) and the flow of HF was increased to 28 cc/min ($4.7 \times 10^{-7}$ m$^3$/s). After 20 minutes, the flow of nitrogen was reduced to 5 cc/min and the flow of HF was increased to 36 cc/min ($6.0 \times 10^{-7}$ m$^3$/s). After 20 minutes, the flow of nitrogen was shut off and the flow of HF was increased to 40 cc/min ($6.7 \times 10^{-7}$ m$^3$/s), and this condition was maintained for 120 minutes. The reactor temperature was adjusted to 350° C. and HF and HCFC-124 vapor were fed to the reactor in molar ratio of 2:1 at a contact time of 3.3 seconds. The GC-MS analysis of the reactor effluent is given below.

| Component | Mole % |
|---|---|
| HFC-125 | 71.4 |
| CFC-115 | 440 ppm |
| HCFC-124 | 16.4 |

-continued

| Component | Mole % |
|---|---|
| HCFC-124a | 0.2 |
| HCFC-133a | 0.3 |
| FCFC-114a | 0.2 |
| HCFC-123 | 11.3 |

Examples 7–9

Additional examples of the conversion of HCFC-124 to HFC-125 are summarized in Table 2 along with the corresponding data for EXAMPLES 1–6. In Table 2, the ppm of 115 is the ppm of 115 relative only to the amount of 125 produced (moles of 115/moles of 125*1000000).

TABLE 2

Product Distribution at 350° C., 3.3 sec CT, and an HF/124 Ratio of 2.0

| Ex. | % Co | % 125 | ppm 115 | % 124 | % 124a | % 133a | % 114a | % 123 | % 113 |
|---|---|---|---|---|---|---|---|---|---|
| C1 | 0 | 77.9 | 2400 | 12.8 | 0.5 | 0 | 0.2 | 7.9 | 0.1 |
| C2 | 10[b] | 19.1 | 48 | 77.5 | 0.4 | | | 3.0 | |
| C3 | 10[b] excess NH$_4$NO$_3$ | 62.0 | 200 | 23.3 | 0.2 | 0.3 | 0.1 | 14.0 | 0.1 |
| 4 | 1 | 76.2 | 1400 | 13.5 | 0.2 | 0.4 | 0.2 | 9.2 | 0.1 |
| 5 | 2 | 74.8 | 780 | 14.9 | 0.2 | 0.3 | 0.2 | 9.5 | 0.1 |
| 6 | 5 excess NH$_4$NO$_3$ | 71.4 | 440 | 16.4 | 0.2 | 0.3 | 0.2 | 11.3 | 0.1 |
| 7 | 2 | 77.6 | 1600 | 12.8 | 0.2 | 0.4 | 0.2 | 8.6 | 0.1 |
| 8 | 3 | 64.8 | n.d.[a] | 22.5 | 0.2 | 0.1 | 0.1 | 12.2 | 0.1 |
| 9 | 5 | 65.8 | 320 | 21.5 | 0.2 | 0.2 | 0.1 | 12.0 | 0.1 |

[a]n.d. means not detected by GC-MS.
[b]As suggested in U.S. Patent Application 60/405,220 [CL2099 US PRV] filed Aug. 22, 2002, these catalysts may be expected to differ significantly from compositions containing lower proportions of Co due to the solubility limit of Co in alpha chromium oxide.

Comparative Examples 10, 17 and 18 and Examples 11–16

In the examples given in Table 3, the reactor temperature was gradually increased from 300° C. to 370° C. while maintaining a contact time of 3.3 seconds and a molar ratio of HF to CHClFCF$_3$ of 2.0. The activity of the various Co-substituted α-Cr$_2$O$_3$ catalysts is compared by determining the temperature where the product contained 70% HFC-125 and the selectivity is compared by determining the amount of CFC-115 in the product at the temperature where the product is 70% HFC-125. The concentration of CFC-115 and the % 125 was monitored at 330° C., well below equilibrium conditions. The catalysts used are from the EXAMPLES 1–9 as noted.

TABLE 3

Activity and Selectivity at 3.3 sec CT, and an HF/124 Ratio of 2.0

| Example | Catalyst from Example. | % Co | ppm 115 @ 70% 125 | Temp ° C. @ 70% 125 | %125 @ 330 C. |
|---|---|---|---|---|---|
| C10 | C1 | 0 | 1000 | 335 | 66 |
| 11 | 4 | 1 | 420 | 335 | 67 |
| 12 | 5 | 2 | 210 | 330 | 70 |
| 13 | 7 | 2 | 550 | 337 | 62 |
| 14 | 8 | 3 | 830 | 363 | 48 |
| 15 | 9 | 5 | 1000 | 358 | 55 |
| 16 | 6 | 5 excess NH$_4$NO$_3$ | 447 | 347 | 59 |
| C17[a] | C2 | 10 | Not active enough[b] | Not active enough[b] | 13 |
| C18[a] | C3 | 10 excess NH$_4$NO$_3$ | Not active enough[b] | Not active enough[b] | 48 |

[a]As suggested U.S. Patent Application 60/405,220 [CL2099 US PRV] filed Aug. 22, 2002, these catalysts may be expected to differ significantly from compositions containing lower proportions of Co due to the solubility limit of Co in alpha chromium oxide.
[b]70% HFC-125 not achieved in this example.

Example 19

Cobalt-substituted chromium oxide (Cr/Co 95/5, 29.04 g, 20 mL, −12 to +20 mesh, (1.68 to 0.84 mm)), prepared as described in PREPARATION EXAMPLE 4 was placed in a ⅝" (1.58 cm) diameter Inconel™ nickel alloy reactor tube heated in a fluidized sand bath. The catalyst was heated from 77° C. to 175° C. in a flow of nitrogen (25 cc/min, 4.2×10$^{-7}$ m$^3$/s) over the course of about 1.2 hours. HF and nitrogen were then co-fed to the reactor at a flow rate of 50 cc/min (8.3×10$^{-7}$ m$^3$/s) each. After 1.5 hours, the nitrogen flow was decreased to 20 cc/min (3.3×10$^{-7}$ m$^3$/s) and the HF flow increased to 80 cc/min (1.3×10$^{-6}$ m$^3$/s). The reactor temperature was gradually increased to 413° C. during a 5 hour period and maintained at 413° C. for an additional 0.6 hour. At the end of this period, the HF flow was stopped and the reactor cooled to 300° C. under nitrogen flow (20 sccm, 3.3×10$^{-7}$ m$^3$/s).

The catalyst prepared as above was placed in the reactor, purged with nitrogen and HF at 300° C. HF and HCFC-123 vapor were co-fed to the reactor in molar ratio of 6:1 at a contact time of 30 seconds. The GC-MS analysis of the reactor effluent is given below.

| Component | Mole % |
|---|---|
| HFC-125 | 26.7 |
| HCFC-124 | 49.2 |
| HCFC-124a | 0.2 |
| CFC-114a | 1.4 |
| HCFC-123 | 22.1 |
| CFC-115 | 0.16 |

Other products included CFC-113a and CFC-113.

What is claimed is:
1. A process for the preparation of pentafluoroethane, comprising:
  (a) contacting a mixture comprising hydrogen fluoride and at least one starting material selected from haloethanes of the formula CX$_3$CHX$_2$ and haloethenes of the formula CX$_2$=CX$_2$, where each X is independently selected from the group consisting of F and Cl provided that no more than four of X are F, with a fluorination catalyst in a reaction zone to produce a product mixture comprising HF, HCl, pentafluoroethane, underfluorinated halogenated hydrocarbon intermediates and less than 0.2 mole percent chloropentafluoroethane based on the total moles of halogenated hydrocarbons in the product mixture;

wherein said fluorination catalyst comprises at least one chromium-containing component selected from (i) a crystalline cobalt-substituted alpha-chromium oxide where from about 0.05 atom % to about 6 atom % of the chromium atoms in the alpha-chromium oxide lattice are replaced by trivalent cobalt, and (ii) a fluorinated crystalline oxide of (i).

2. The process of claim 1 further comprising
(b) separating the product of step (a) to recover $CF_3CHF_2$ as a product and to obtain underfluorinated halogenated hydrocarbon intermediates; and
(c) returning underfluorinated halogenated hydrocarbon intermediates obtained in step (b) back to the step (a) reaction zone;

* * * * *